US008759589B2

(12) United States Patent
Göttel et al.

(10) Patent No.: US 8,759,589 B2
(45) Date of Patent: *Jun. 24, 2014

(54) METHODS OF SYNTHESIZING 2-METHOXYMETHYL-1,4-BENZENEDIAMINE

(75) Inventors: Otto Richard Göttel, Marly (CH); Wolfram Geibel, Huenfeld (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/248,696

(22) Filed: Sep. 29, 2011

(65) Prior Publication Data

US 2012/0130128 A1 May 24, 2012

Related U.S. Application Data

(60) Provisional application No. 61/387,712, filed on Sep. 29, 2010.

(51) Int. Cl.
*C07C 213/00* (2006.01)

(52) U.S. Cl.
USPC ........................................................ 564/418

(58) Field of Classification Search
None
See application file for complete search history.

(56) References Cited

U.S. PATENT DOCUMENTS

| 2,273,564 | A |   | 2/1942  | Dickey |          |
| 4,997,451 | A |   | 3/1991  | Clausen |         |
| 6,648,923 | B1 |  | 11/2003 | Goettel |         |
| 7,445,645 | B2 |  | 11/2008 | Sabelle |         |
| 2012/0078016 | A1 | * | 3/2012 | Gardlik et al. | ................ 564/355 |

FOREIGN PATENT DOCUMENTS

| DE | EP-0307817 | * | 9/1988 | .................... 534/617 |
| DE | 3731202 A1 | | 7/1989 | |
| JP | 11012239 | | 1/1999 | |

OTHER PUBLICATIONS

Finkelstein Reaction—Wikipedia Oct. 22, 2010, pp. 1-2.

* cited by examiner

*Primary Examiner* — Clinton Brooks
(74) *Attorney, Agent, or Firm* — James T. Fondriest

(57) ABSTRACT

Disclosed is a method of making 2-methoxymethyl-1,4-benzenediamine that includes hydrogenating 1-benzylamino-2-(methoxymethyl)-4-nitrobenzene in the presence of a hydrogenation catalyst.

15 Claims, No Drawings

METHODS OF SYNTHESIZING 2-METHOXYMETHYL-1,4-BENZENEDIAMINE

CROSS REFERENCE TO RELATED APPLICATION

This application claims the benefit of U.S. Provisional Application No. 61/387,712 filed Sep. 29, 2010.

FIELD OF THE INVENTION

The subject matter of the present application relates to the synthesis of 2-methoxymethyl-1,4-benzenediamine and physiologically compatible salts thereof.

BACKGROUND OF THE INVENTION

2-Methoxymethyl-1,4-benzenediamine ("MBB") and physiologically compatible salts thereof are useful as primary intermediates in oxidative hair color. A current process for synthesizing MBB may be accomplished as discussed in U.S. Pat. No. 4,997,451 (discussing steps 1 and 2 of the below-detailed process) and U.S. Pat. No. 6,648,923 (discussing steps 3-6 of the below-detailed process). Such a process is illustrated by the following reaction scheme:

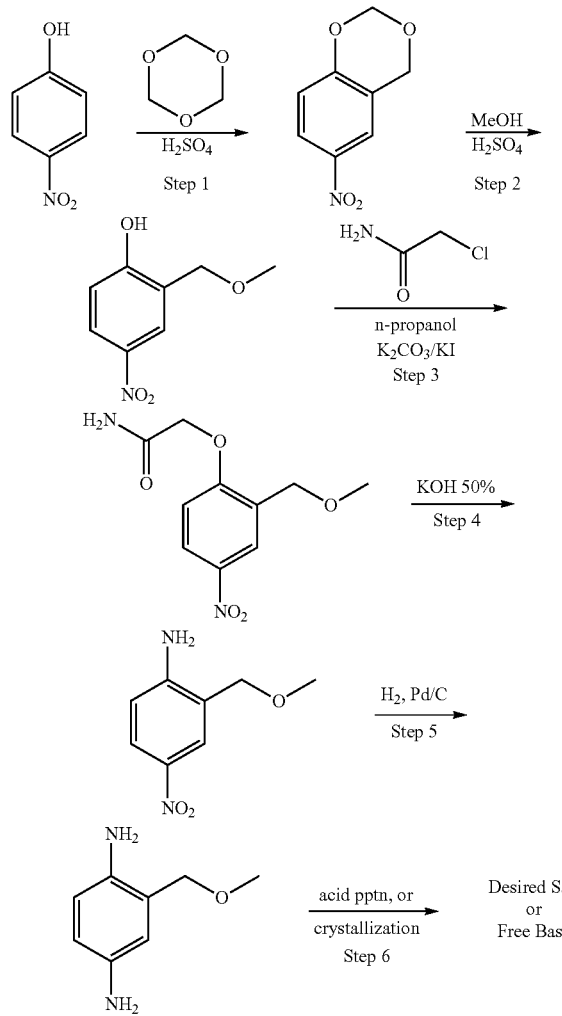

As detailed in step 2 of the reaction scheme, it is inherent in the methodology that the intermediate product 6-nitro-4H-benzo[d][1,3]dioxine be exposed to sulfuric acid in order to form the methoxymethyl side chain in the molecule. However, exposure of 6-nitro-4H-benzo[d][1,3]dioxine to such acidic conditions also leads to the formation of 2-hydroxymethyl-4-nitrophenol, a precursor of an undesired by-product 2-hydroxymethyl-1,4-diaminobenzene ("Oxytol A"). The removal of 2-hydroxymethyl-4-nitrophenol through additional recrystallization steps leads to lower overall MBB yields and higher manufacturing costs when compared to other known processes, such as the one in the above-detailed reaction scheme. Accordingly, new methods of making MBB are of continued interest.

SUMMARY OF THE INVENTION

One embodiment of a method of making 2-methoxymethyl-1,4-benzenediamine includes hydrogenating 4-nitro-2-methoxymethyl-1-benzylaminobenzene in the presence of a hydrogenation catalyst.

One embodiment of a method of making 2-methoxymethyl-1,4-benzenediamine from 2-chlorobenzylchloride includes nitrating the 2-chlorobenzylchloride to obtain 4-nitro-2-chloromethyl-chlorobenzene, introducing a methoxymethyl group to the 4-nitro-2-chloromethyl-chlorobenzene to obtain 4-nitro-2-methoxymethyl-chlorobenzene, introducing a benzylamine group to the 4-nitro-2-methoxymethyl-chlorobenzene to obtain 4-nitro-2-methoxymethyl-1-benzylaminobenzene, and hydrogenating the 4-nitro-2-methoxymethyl-1-benzylaminobenzene in the presence of a hydrogenation catalyst to obtain the 2-methoxymethyl-1,4-benzenediamine.

Another embodiment of a method of making 2-methoxymethyl-1,4-benzenediamine from 2-chlorobenzylchloride includes nitrating the 2-chlorobenzylchloride to obtain 4-nitro-2-chloromethyl-chlorobenzene.

DETAILED DESCRIPTION OF THE INVENTION

It has now been surprisingly found that the 2-methoxymethyl-1,4-benzenediamine ("MBB") shown in formula (I):

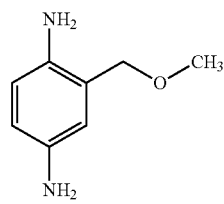

is obtainable from the 2-chlorobenzylchloride shown in formula (II):

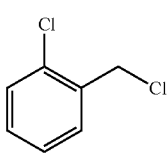

in a simple manner with a good overall yield.

Accordingly, a method for making the MBB shown in formula (I) from the 2-chlorobenzylchloride shown in formula (II) comprises the following reaction scheme:

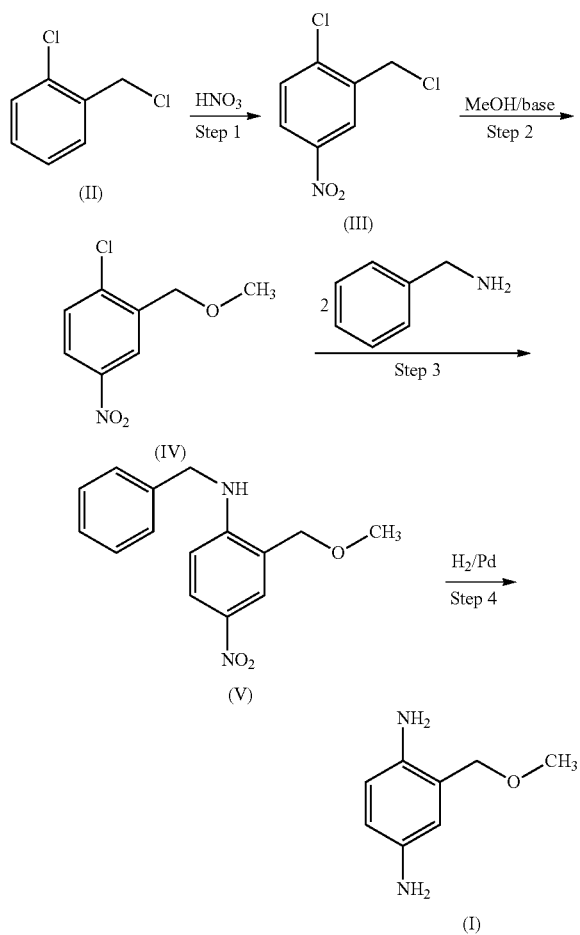

Step 1: The Nitrating Step

Step 1 of the reaction scheme comprises nitrating the 2-chlorobenzylchloride shown in formula (II) to obtain the 4-nitro-2-chloromethyl-chlorobenzene intermediate product shown in formula (III). Such a nitrating step is described in the disclosure of German Patent Publication No. 3731202 of Jul. 13, 1989, the entirety of which is fully incorporated herein by reference.

Step 2: The Methoxymethyl Step

Step 2 of the reaction scheme comprises introducing a methoxymethyl group to the 4-nitro-2-chloromethyl-chlorobenzene intermediate product shown in formula (III) to obtain the 4-nitro-2-methoxymethyl-chlorobenzene intermediate product shown in formula (IV) through nucleophilic displacement. A solution of alkali methoxide and/or alkali hydroxide in methanol may provide the methoxymethyl group. Non-limiting examples of suitable alkali methoxides include sodium methoxide, lithium methoxide and potassium methoxide. Non-limiting examples of suitable alkali hydroxides include sodium hydroxide and potassium hydroxide. The concentration of alkali methoxide and/or alkali hydroxide in methanol ranges from about 10% to about 30%, more typically about 20%.

Embodiments of step 2 may include mixing the 4-nitro-2-chloromethyl-chlorobenzene with the alkali methoxide and/or alkali hydroxide solution, heating under reflux in methanol and stirring the mixture at this temperature for a period of about 30 minutes to about 2 hours. Other embodiments of step 2 further include an additional sub-step of first dissolving the 4-nitro-2-chloromethyl-chlorobenzene in methanol before mixing with the alkali methoxide and/or alkali hydroxide solution.

Because the introduction of a methoxymethyl group to the 4-nitro-2-chloromethyl-chlorobenzene occurs under non-hydrolyzing conditions, the formation of 2-hydroxymethyl-4-nitrophenol (i.e., a precursor of the undesired by-product 2-hydroxymethyl-1,4-diaminobenzene) is avoided. Accordingly, additional recrystallization steps at this stage of MBB synthesis are unnecessary compared to known synthesis steps.

Step 3: The Benzylamine Step

Step 3 of the reaction scheme comprises introducing benzylamine to the 4-nitro-2-methoxymethyl-chlorobenzene intermediate product shown in formula (IV) to obtain the 1-benzylamino-2-(methoxymethyl)-4-nitrobenzene intermediate product shown in formula (V) through nucleophilic displacement. Normally, only aromatic fluoro atoms can be displaced, but with the specific substitution pattern detailed herein, the chloro atom also has sufficient activity to be displaced. Alternatively, the chloro atom can be exchanged for a fluoro atom, (for example, but not limited to, by using potassium fluoride and 18-crown-6), either in situ during the reaction with benzylamine, or in a discrete step prior to treatment with benzylamine. See Finkelstein, H. *Ber.*, 1910, 43, 1528, the entire disclosure of which is fully incorporated herein by reference.

Embodiments of step 3 may include mixing the 4-nitro-2-methoxymethyl-chlorobenzene with benzylamine at a molar ratio within a range of about 1:2 to about 1:5, more typically about 1:3. The reaction typically occurs at a temperature within a range of about 100° C. to about 180° C., more typically about 120° C. to about 150° C., and is completed over a time period of about 30 minutes to about 4 hours. Although embodiments of step 3 are typically carried out without the use of a solvent, some embodiments may utilize a solvent such as dimethylformamide, dimethylacetamide, N-methylpyrrolidone or dimethylsulfoxide.

In addition, embodiments of step 3 may be carried out with or without the presence of a phase-transfer catalyst. For embodiments of step 3 that are carried out in the presence of a phase transfer catalyst, suitable phase transfer catalysts may comprise ammonium salts that include, but are not limited to, tetrapentylammonium bromide, tetraoctylammonium chloride, tetraoctylammonium bromide, tetrahexylammonium iodide, tetrahexylammonium chloride, tetrahexylammonium bromide, tetraheptylammonium bromide, tetraethylammonium tetrafluoroborate, tetraethyl ammonium chloride, tetraethylammonium bromide, tetradodecylammonium tetrafluoroborate, tetradodecylammonium chloride, tetradodecylammonium bromide, tetradecyl-trimethylammonium chloride, phenyl-trimethylammonium bromide, octyl-trimethyl ammonium bromide, octadecyl-trimethylammonium chloride, octadecyl-trimethylammonium bromide and methyl-trioctylammonium iodide. The catalyst may be typically present with the 1-benzylamino-2-(methoxymethyl)-4-nitrobenzene in a molar ratio within the range of about 0.01:1 to about 10:1, more typically about 0.5:1 to about 1.5:1, and more typically about 1:1.

Embodiments of step 3 may also include a sub-step of isolating the 1-benzylamino-2-(methoxymethyl)-4-nitrobenzene. Isolating the 1-benzylamino-2-(methoxymethyl)-4-nitrobenzene may be carried out by pouring the reaction mixture into toluene and water to yield a two-phase system, and then acidifying that two-phase system through the addition of an acid. Suitable acids include hydrochloric acid, sulphuric acid, phosphoric acid, acetic acid, citric acid, boric acid, and alkali dihydrogenophosphates. In some embodiments, the acid solution is prepared in advance and overlaid with toluene to provide a two-phase system, and the reaction mixture is added to this two-phase system. The acid is typically added at a concentration sufficient to yield a pH of about 0.5 to about 5, more typically a pH of about 1 to about 4. Upon adding the reaction mixture to the two-phase system, the 1-benzylamino-2-(methoxymethyl)-4-nitrobenzene passes into the organic layer. After separating the organic layer from the aqueous layer, the aqueous layer is discarded and the organic layer is cooled down to about 40° C., wherein the 1-benzylamino-2-(methoxymethyl)-4-nitrobenzene crystallizes out and may be isolated by filtration.

Step 4: The Hydrogenating Step

Step 4 of the reaction scheme comprises hydrogenating the 1-benzylamino-2-(methoxymethyl)-4-nitrobenzene intermediate product shown in formula (V) in the presence of a hydrogenation catalyst (e.g., a palladium or platinum based catalyst) to obtain the 2-methoxymethyl-1,4-benzenediamine shown in formula (I). In this reaction step, the reducing of the nitro group occurs before the cleaving of the benzylamino group.

Embodiments of step 4 may include mixing the 1-benzylamino-2-(methoxymethyl)-4-nitrobenzene with a hydrogenation catalyst and a solvent (resulting in an exothermic reaction which may be controlled by external cooling), applying a hydrogen atmosphere of about 2 to 3 bar pressure over the reaction mixture and stirring the mixture under hydrogen atmosphere at this temperature for a period of about 30 minutes to about 4 hours. In addition, embodiments of step 4 may further include the sub-steps of filtering, washing and drying the 2-methoxymethyl-1,4-benzenediamine. Alternatively, the reaction mixture may be heated under an atmosphere of hydrogen to a temperature within a range of about 20° C. to about 78.4° C., more typically about 60° C. to about 78.4° C. In addition, embodiments of step 4 may further include the sub-steps of filtering, washing and drying the 2-methoxymethyl-1,4-benzenediamine.

The catalytic hydrogenation reaction of step 4 may occur in a hydrogenation solvent selected from a group including, but not limited to, ethyl acetate, toluene, butyl acetate, ethanol and methanol. Moreover, in some embodiments, a subsequent crystallization step can also be carried out in the same solvent utilized in this catalytic hydrogenation step (e.g., toluene), because the hydrophobic benzylamino group provides excellent solubility to the intermediate product of formula (V). Thus, in embodiments that utilize an optional crystallization step after the hydrogenating step, solvent replacement in the crystallization step may be avoided.

Optional Step 5: The Acid Precipitating Step

Optional step 5 of the reaction scheme comprises acid precipitating the 2-methoxymethyl-1,4-benzenediamine shown in formula (I) to obtain a specifically desired salt. Embodiments of step 5 may include adding the 2-methoxymethyl-1,4-benzenediamine to an acid solution that contains a reductant (e.g., sodium sulfite) to prevent oxidations, while utilizing external cooling to maintain the reaction at a temperature within a range of about 0° C. to about 40° C., more typically about 10° C. to about 30° C., over a period of about 30 minutes to 3 hours until the salt crystallizes out of the solution. Non-limiting examples of suitable acid solutions include malic acid, sulfuric acid, hydrochloric acid, phosphoric acid and tartaric acid. In addition, embodiments of step 5 may further include the sub-steps of filtering, washing and drying the salt of 2-methoxymethyl-1,4-benzenediamine.

The following examples illustrate the above-described syntheses, but do not limit the broad concept of the invention.

Example 1

Preparation of 2-methoxymethyl-1,4-benzenediamine

Step 1: The Nitrating Step

Step 1 details the preparation of 4-nitro-2-chloromethyl-chlorobenzene. 50.0 g (0.31 mol) of 2-chlorobenzyl chloride is dissolved in 141 ml of concentrated sulfuric acid and cooled in an ice/methanol bath to an internal temperature of −5° C. 20.66 g (0.328 mol) of fuming nitric acid is placed in an attached addition funnel. The nitric acid is added at such a rate as to keep the internal temperature below 0° C. Near the end of the reaction the product crashes from the solution and stirring ceases. Thin layer chromatography ("TLC") analysis indicates the reaction is, nonetheless, complete. The reaction mixture is poured over 750 ml of ice in a 1 L Erlenmeyer flask. Additional ice is added to keep reaction cold. The cold reaction is allowed to stand so that the solids settle. The supernant is poured off. The solid is triturated one additional time with 250 ml water. The final solid is taken up in 400 ml dichloromethane and washed with two (2) 200 ml portions of saturated sodium bicarbonate solution. The dichloromethane phase is then dried (sodium sulfate), filtered and evaporated. The product, 4-nitro-2-chloromethyl-chlorobenzene (56 g, 0.272 mol) is obtained in 88% as a semi-solid and used 'AS IS' in Step 2.

$^1$H-NMR (CDCl3): 8.41 (d), 1H, 8.17 (dd) 1H, 7.594 (d), 1H, 4.756 (s), 2H.

Step 2: The Methoxymethyl Step

Step 2 details the preparation of 4-nitro-2-methoxymethyl-chlorobenzene.

Embodiment A

Utilizing an Alkali Methoxide 15.0 g (72.8 mmol) of 4-nitro-2-chloromethyl-chlorobenzene are stirred in 50 ml of anhydrous methanol. At room temperature, 13.9 g of a of a sodium methoxide solution (30% in methanol) is added. In the course of the addition, sodium chloride precipitates out and a colorless to rose-colored suspension is obtained. The addition of the sodium methoxide solution is finished after 30 minutes, whereas the internal temperature rises to approximately 30° C. Then the reaction mixture is heated for 30 minutes under reflux, and the suspension is filtered hot to obtain a clear solution. Upon cooling, the product, 4-nitro-2-methoxymethyl-chlorobenzene, crystallizes out and is filtered off. The product yield is 11.0 g of a yellowish solid. The filtrate is concentrated to approximately half of the volume and cooled in an ice bath to give another 3.8 g of product. The total product yield is 14.8 g.

$^1$H-NMR (DMSO-$d_6$): 8.27 (d), 1H, 8.18 (dd), 1H, 7.77 (d), 1H, 4.58 (s), 2H, 3.44 ppm (s), 3H.

Embodiment B

Utilizing an Alkali Hydroxide 180.0 g of 4-nitro-2-chloromethyl-chlorobenzene are stirred in 450 ml of anhydrous methanol. After heating to reflux, a prepared solution of 41.9 g of sodium hydroxide in 270 ml of methanol is added over a period of one hour. In order to complete the reaction the mixture is stirred under reflux for an additional hour. In the course of the addition, sodium chloride precipitates out and a yellowish suspension is obtained. After completion of the reaction, the suspension is cooled in an ice bath. Under continuous cooling at less than 10° C., a solution of 90 ml acetic acid in 540 ml water is added within 15 minutes. After addition, the suspension is stirred in an ice bath for an additional 30 minutes. Finally, the reaction product, 4-nitro-2-methoxymethyl-chlorobenzene, is filtered off and washed with a mixture of water and methanol (9:1). The product is dried at 40° C. The product yield is 165.4 g.

Step 3: The Benzylamine Step

Step 3 details the preparation of 1-benzylamino-2-(methoxymethyl)-4-nitrobenzene. 50.0 g of 4-nitro-2-methoxymethyl-chlorobenzene and 52.12 g of tetraethylammonium bromide are stirred in 79.72 g of benzylamine. After heating to approximately 125° C., the reaction is stirred for 5 hours. In the course of the reaction the red suspension changes to a red solution. After completion of the reaction the solution is slightly cooled down. 200 ml of toluene is added, followed by a solution of 35 ml hydrochloric acid (25% in 150 ml of water) forming a yellow emulsion. After cooling to room temperature, the formed layers are separated. The aqueous layer is washed twice, with each wash using 50 ml of toluene. The combined organic layers containing 1-benzylamino-2-(methoxymethyl)-4-nitrobenzene are washed twice, with each wash using 50 ml of water containing 5 g of sodium chloride. After washing, the organic layer is reduced under vacuum to dryness. The residue is dissolved in 300 ml of ethanol under heating to form a yellow to red solution. Then the solution is cooled down to room temperature. At approximately 25° C., a small part of the product slowly crystallises out. When the crystallisation has started, 150 ml of water is added over a 30 minute period to complete the precipitation. After stirring for 30 minutes at room temperature, the product, containing 1-benzylamino-2-(methoxymethyl)-4-nitrobenzene, is filtered off and washed with a mixture of water and ethanol (6:4). The product is dried at 40° C. The product yield is 57.5 g.

$^1$H-NMR (DMSO-$d_6$): 8.15 (d), 1H, 7.94 (dd), 1H, 7.31 (m), 4H, 7.22 (m), 1H, 7.14 (t), 1H, 6.55 (d), 1H, 4.52 (t), 2H, 4.46 (s), 2H, 3.36 ppm (s), 3H.

Step 4: The Hydrogenating Step

Step 4 details the preparation of 2-methoxymethyl-1,4-benzenediamine as a free base. 20.0 g of 1-benzylamino-2-(methoxymethyl)-4-nitrobenzene, 0.4 g of palladium (10% on carbon containing approximately 50% by weight water) and 15 g of magnesium sulphate are suspended in 60 ml of toluene. After heating to approximately 60-80° C., the reaction is stirred under hydrogen atmosphere of 2-3 bar pressure for 30 minutes. In the course of the reaction, the yellowish grey suspension turns to a darker grey suspension. Due to the sensitivity of the final product to oxygen, the following steps are carried out under inert gas atmosphere. After completion of the reaction, the hot suspension is filtered. The filtration residue is washed twice, with each wash using 20 ml of toluene. After filtration, the solution is cooled down and stirred for 30 minutes at 0-3° C. The product, 2-methoxymethyl-1,4-benzenediamine, is filtered off and washed three times, with each wash using 10 ml of cold toluene. The product is dried at 60° C. under vacuum. The product yield is 8.5 g.

$^1$H-NMR (DMSO-$d_6$): 6.41 (d), 1H, 6.37 (d), 1H, 6.33 (dd), 1H, 4.24 (s), 2H, 4.21 (s), 2H, 4.11 (s), 2H, 3.23 ppm (s), 3H.

Example 2

Preparation of 2-methoxymethyl-1,4-benzenediamine as an Adduct with Malic Acid

Step 5: The Acid Precipitating Step

Step 5 details the further preparation of the 2-methoxymethyl-1,4-benzenediamine as an adduct with malic acid. The 2-methoxymethyl-1,4-benzenediamine of Example 1 is combined with the washing liquid under an inert gas atmosphere to form a solution. That solution is added to a second solution of 66.7 g (0.483 mol) D,L-malic acid and 0.4 g sodium sulfite dissolved in a mixture of 320 ml ethanol and 40 ml water. The addition is carried out over a time period of about 30 minutes. After the addition of about 50%, the final product starts to crystallize out. After the addition is completed, the obtained yellowish suspension is allowed to cool down to room temperature with stirring, which takes another 30 minutes. Thereafter, the precipitate is filtered off and washed four times, with each wash using 60 ml of ethanol. The product is dried at 60° C. under vacuum. The product yield is 109 g.

Nuclear magnetic resonance ("NMR") sprectra are in accordance with the chemical structure and show the characteristic signal patterns of malic acid and 2-methoxymethyl-1,4-benzenediamine. Titration with perchloric acid and sodium hydroxide confirm the 1:1 stoichiometry of 2-methoxymethyl-1,4-benzenediamine with malic acid.

Elemental analysis ($C_8H_{12}N_2O \cdot C_4H_6O_5$, 286.29):

|  | % C | % H | % N |
|---|---|---|---|
| calculated: | 50.35 | 6.34 | 9.79 |
| found: | 50.13 | 6.26 | 9.66 |

While the syntheses detailed herein have been described in embodiments of methods of making 2-methoxymethyl-1,4-benzenediamine and physiologically compatible salts thereof, such syntheses are not intended to be limited to the details shown, since various modifications and changes may be made without departing in any way from the spirit of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making 2-methoxymethyl-1,4-benzenediamine comprising hydrogenating 1-benzylamino-2-(methoxymethyl)-4-nitrobenzene in the presence of a hydrogenation catalyst.

2. The method of claim 1, wherein the hydrogenation catalyst is palladium or platinum based.

3. The method of claim 1, wherein the hydrogenating occurs in a hydrogenation solvent selected from a group comprising ethyl acetate, toluene, butyl acetate, ethanol and methanol.

4. The method of claim 1, wherein the 1-benzylamino-2-(methoxymethyl)-4-nitrobenzene is obtained by introducing benzylamine to 4-nitro-2-methoxymethyl-chlorobenzene.

5. The method of claim 4, wherein the introduction of benzylamine occurs in the presence of a phase transfer catalyst.

6. The method of claim 5, wherein the phase transfer catalyst is tetraethylammonium bromide.

7. The method of claim 4, wherein the 4-nitro-2-methoxymethyl-chlorobenzene is obtained by introducing a methoxymethyl group to 4-nitro-2-chloromethyl-chlorobenzene.

8. The method of claim 7, wherein the introduction of the methoxymethyl group occurs by nucleophilic displacement.

9. The method of claim 7, wherein the 4-nitro-2-chloromethyl-chlorobenzene is obtained by nitrating 2-chlorobenzylchloride.

10. A method of making 2-methoxymethyl-1,4-benzenediamine from 2-chlorobenzylchloride comprising:
    a) nitrating the 2-chlorobenzylchloride to obtain 4-nitro-2-chloromethyl-chlorobenzene;
    b) introducing a methoxymethyl group to the 4-nitro-2-chloromethyl-chlorobenzene to obtain 4-nitro-2-methoxymethyl-chlorobenzene;
    c) introducing a benzylamine group to the 4-nitro-2-methoxymethyl-chlorobenzene to obtain 1-benzylamino-2-(methoxymethyl)-4-nitrobenzene; and
    d) hydrogenating the 1-benzylamino-2-(methoxymethyl)-4-nitrobenzene in the presence of a hydrogenation catalyst to obtain the 2-methoxymethyl-1,4-benzenediamine.

11. The method of claim 10, wherein the hydrogenation catalyst is palladium or platinum based.

12. The method of claim 10, wherein the hydrogenating occurs in a hydrogenation solvent selected from a group comprising ethyl acetate, toluene, butyl acetate, ethanol and methanol.

13. The method of claim 10, wherein the introducing of benzylamine occurs in the presence of a phase transfer catalyst.

14. The method of claim 13, wherein the phase transfer catalyst is tetraethylammonium bromide.

15. The method of claim 10, wherein the introducing of the methoxymethyl group to the 4-nitro-2-chloromethyl-chlorobenzene occurs by nucleophilic displacement.

\* \* \* \* \*